US009782346B2

(12) United States Patent
Venkatraman et al.

(10) Patent No.: US 9,782,346 B2
(45) Date of Patent: Oct. 10, 2017

(54) BIODEGRADABLE OCULAR IMPLANT

(71) Applicants: Nanyang Technological University, Singapore (SG); Singapore Health Services Pte Ltd, Singapore (SG)

(72) Inventors: Subramanian Venkatraman, Singapore (SG); Yin Chiang Freddy Boey, Singapore (SG); Tina Wong, Singapore (SG); Jodhbir Metha, Singapore (SG)

(73) Assignees: Nanyang Technological University, Singapore (SG); Singapore Health Services PTE LTD, Singapore (SG)

( * ) Notice: Subject to any disclaimer, the term of this patent is extended or adjusted under 35 U.S.C. 154(b) by 0 days.

(21) Appl. No.: 14/862,963

(22) Filed: Sep. 23, 2015

(65) Prior Publication Data

US 2016/0206556 A1   Jul. 21, 2016

Related U.S. Application Data

(63) Continuation of application No. 13/816,637, filed as application No. PCT/SG2011/000282 on Aug. 12, 2011, now abandoned.
(Continued)

(51) Int. Cl.
*A61K 9/24* (2006.01)
*A61K 9/00* (2006.01)
(Continued)

(52) U.S. Cl.
CPC .......... *A61K 9/0051* (2013.01); *A61F 9/0017* (2013.01); *A61K 9/1647* (2013.01); *A61K 31/19* (2013.01); *A61K 31/5575* (2013.01); *A61K 31/573* (2013.01); *A61K 47/34* (2013.01); *A61L 27/18* (2013.01); *A61L 27/54* (2013.01); *A61L 27/58* (2013.01); *A61L 31/125* (2013.01); *A61L 31/148* (2013.01); *B05D 5/00* (2013.01); *B29C 39/02* (2013.01); *B29C 39/025* (2013.01); *B29D 11/023* (2013.01); *A61L 2430/16* (2013.01); *B29K 2067/04* (2013.01); *B29K 2067/046* (2013.01); *B29K 2105/0035* (2013.01);
(Continued)

(58) Field of Classification Search
CPC .. A61K 9/0051; A61K 9/1647; A61K 31/573; A61F 9/0017
See application file for complete search history.

(56) References Cited

U.S. PATENT DOCUMENTS

2006/0024350 A1 * 2/2006 Varner .................. A61F 9/0017
424/427

FOREIGN PATENT DOCUMENTS

WO       2010/059214       *  5/2010
WO   WO 2010/059214 A2      5/2010

OTHER PUBLICATIONS

Baudouin, C. et al., *Short Term Comparative Study of Topical 2% Carteolol With and Without Benzalkonium Chloride in Healthy Volunteers*, Br J Ophthalmol 82 (1998) 39-42.
(Continued)

*Primary Examiner* — Carlos Azpuru
(74) *Attorney, Agent, or Firm* — Alston & Bird LLP

(57) ABSTRACT

Provided is a biodegradable ocular implant for sustained drug delivery, including a first layer comprising a first biodegradable polymer, wherein the first layer contains a drug dispersed or dissolved therein. A multi-layered biodegradable ocular implant is also disclosed.

53 Claims, 11 Drawing Sheets

Related U.S. Application Data

(60) Provisional application No. 61/372,959, filed on Aug. 12, 2010.

(51) Int. Cl.

| | | |
|---|---|---|
| *A61K 9/16* | (2006.01) | |
| *A61F 9/00* | (2006.01) | |
| *A61L 31/12* | (2006.01) | |
| *A61L 31/14* | (2006.01) | |
| *B05D 5/00* | (2006.01) | |
| *A61K 47/34* | (2017.01) | |
| *A61L 27/18* | (2006.01) | |
| *A61L 27/54* | (2006.01) | |
| *A61L 27/58* | (2006.01) | |
| *A61K 31/19* | (2006.01) | |
| *A61K 31/5575* | (2006.01) | |
| *A61K 31/573* | (2006.01) | |
| *B29C 39/02* | (2006.01) | |
| *B29D 11/02* | (2006.01) | |
| *C08L 67/04* | (2006.01) | |
| *C08L 69/00* | (2006.01) | |
| *B29K 67/00* | (2006.01) | |
| *B29K 105/00* | (2006.01) | |

(52) U.S. Cl.
CPC .......... *B29K 2105/0073* (2013.01); *B29K 2995/006* (2013.01); *B29K 2995/0056* (2013.01); *C08L 67/04* (2013.01); *C08L 69/005* (2013.01)

(56) References Cited

OTHER PUBLICATIONS

Carcaboso, A. M. et al., *Episcleral Implants for Topotecan Delivery to the Posterior Segment of the Eye*, Investigative Ophthalmology & Visual Science, vol. 51, No. 4 (2010), 2126-2134.

Dong, X. et al., *Intravitreal Implantation of the Biodegradable Cyclosporine A Drug Delivery System for Experimental Chronic Uveitis*, Graefe's Arch. Clin. Exp. Ophthalmol., vol. 244 (2006) 492-497.

Herreras, J. M. et al., *Ocular Surface Alteration After Long-Term Treatment With an Antiglaucomatous Drug*, Ophthalmology 99(7), (1992) 1082-1088.

International Preliminary Report on Patentability (Chapter II) from International Application No. PCT/SG2011/000282, dated Jul. 11, 2012.

International Search Report and Written Opinion for Application No. PCT/SG2011/000282 dated Nov. 29, 2011.

Kim, Y-M. et al., *A Novel Design of One-Side Coated Biodegradable Intrascleral Implant for the Sustained Release of Triamcinolone Acetonide*, European Journal of Pharmaceutics and Biopharamaceutics, vol. 70 (2008) 179-186.

Lazdina, B. et al., *Synthesis and Properties of Cross-Linked Poly-(ester urethanes) from Poly(lactide) Triols and Poly(caprolactone) Diols*, Proc. Estonian Acad. Sci. Chem., vol. 55, No. 2 (2006) 85-92.

Leung, E. W. et al., *Prevalence of Ocular Surface Disease in Glaucoma Patients*, J Glaucoma, vol. 17, No. 5, (Aug. 2008) 350-355.

Office Action for corresponding U.S. Appl. No. 13/816,637 dated Mar. 23, 2015.

Peng, Y. et al., *Biocompatibility and Biodegradation Studies of Subconjunctival Implants in Rabbit Eyes*, Plos One, vol. 6, No. 7, e22507, (Jul. 2011).

Quigley, H.A. et al., *The Number of People With Glaucoma Worldwide in 2010 and 2020*, Br J Ophthalmol 90 (2006) 262-267.

Shi, W. et al., *Sustained Intraocular Rapamycin Delivery Effectively Prevents High-Risk Corneal Allograft Rejection and Neovasularization in Rabbits*, Investigative Ophthalmology & Visual Science, vol. 47, No. 8 (2006) 3339-3344.

*The Advanced Glaucoma Intervention Study (AGIS): 7. The Relationship Between Control of Intraocular Pressure and Visual Field Deterioration*, American Journal of Ophthalmology, vol. 130, No. 4 (Oct. 2000) 429-440.

Wilson, W. S. et al., *Effect of Benzalkonium Chloride on the Stability of the Precorneal Tear Film in Rabbit and Man*, Brit. J. Ophthal. 59 (1975) 667-669.

Yee, R. W., *The Effect of Drop Vehicle on the Efficacy and Side Effects of Topical Glaucoma Therapy: A Review*, Current Opinion in Ophthalmology 18 (2007) 134-139.

\* cited by examiner (A)

(B)

BIODEGRADABLE OCULAR IMPLANT

CROSS-REFERENCE TO RELATED APPLICATION

This application is a continuation of U.S. application Ser. No. 13/816,637, filed May 2, 2013, which is a national phase entry of International Application No. PCT/SG2011/000282, filed Aug. 12, 2011, which claims the benefit of U.S. Provisional Application No. 61/372,959, filed Aug. 12, 2010, the entire contents of which are incorporated herein by reference.

TECHNICAL FIELD

Various embodiments relate to the field of ocular implants for drug delivery, in particular biodegradable ocular implants.

BACKGROUND

The eye is a vital organ that provides sight, which is both anatomically and immunologically privileged. This means that while the organ is protected physiologically, it is also resistant to penetration by foreign substances such as drugs. Ocular drug delivery development has led to a multitude of approaches and systems that vary in mode of administration, implantation site, composition and vehicles. Such systems aim to circumvent the problems of drug bioavailability, sustainability and feasibility of the system as well as reduce the effect of the single major cause of poor therapeutic response from poor patient compliance.

There are many diseases of the eye that require constant administration of a bioactive agent, either life-long such as in the treatment of glaucoma or in severe ocular surface immune disorders, or for prolonged periods (months) such as after surgery.

Full thickness corneal transplantation (Penetrating keratoplasty (PK)) has been the standard surgical treatment for corneal blindness for many years. Improvements over the last quarter of a century in surgical instrumentation and transplantation techniques, and advancements in the management of immune rejection, post-operative inflammation, cataracts and glaucoma have lead to steady improvements in corneal graft survival.

Despite these advances, the long-term outcome of PK still remains far from ideal; data from corneal graft registries of industrialized countries suggest that the overall 10-year survival rate may be as low as 50%, whilst the Singapore Cornea Transplant Study (SCTS) found that the overall 10-year survival of optical grafts to be no better for Asian patients (52.0%). Following corneal transplantation, patients require intensive steroid medication for at least one year. The development of sustained release steroid formulation will significantly improve drop compliance post keratoplasty. In high risk cases, steroid therapy is supplemented by the use of steroid sparing immune-modulating agents e.g. cyclosporine, mycophenolate. The development of sustained drug release formulations of these drugs will aid in compliance and contribute to long-term graft survival in these high risk cases. The development of a sustained release anti-angiogenic drugs will aid in reducing the preoperative effects of multiple quadrant corneal vascularization and hence improve corneal graft survival. The mainstay of treatment involves the use of intensive topical steroids. The development of a sustained release steroid releasing delivery device will significantly improve drop compliance in cases of graft rejection.

Several other ocular surface disease e.g. vernal keratoconjunctivits, allergic eye disease, require the chronic use of intensive immunosuppressants. The development of sustained release steroids as well as other immunosuppressant agents will allow for better control of these inflammatory ocular surface diseases.

Sustained delivery for antibiotics, anti-inflammatories, anti-scarring as well as anti-glaucoma medications would revolutionise ophthalmic medical therapy.

SUMMARY

The present invention aims to provide a biodegradable ocular implant for sustained drug delivery that overcomes the above disadvantages.

In a first aspect, a biodegradable ocular implant for sustained drug delivery is provided. The implant comprises a first layer comprising a first biodegradable polymer, wherein the first layer contains a drug dispersed or dissolved therein.

In a second aspect, a method of forming a biodegradable ocular implant for sustained drug delivery is provided. The method comprises:
(a) providing a first layer comprising a first biodegradable polymer; and
(b) loading the first biodegradable polymer with a drug.

In a third aspect, a method for treating an ocular disease or reducing preoperative effects of multiple quadrant corneal vascularization or improving corneal graft survival is provided. The method comprises implanting the present biodegradable ocular implant to a subject in need thereof.

In another aspect, the use of a biodegradable ocular implant for the treatment of an ocular disease or reducing preoperative effects of multiple quadrant corneal vascularization or improving corneal graft survival is provided.

In a further aspect, a biodegradable ocular implant for sustained drug delivery, comprising a first layer comprising a first biodegradable polymer matrix capable of containing a drug dispersed or dissolved therein is provided.

In yet another aspect, a multi-layered biodegradable ocular implant for sustained drug delivery is provided. The multi-layered implant comprises:
(a) a first layer comprising a first biodegradable polymer capable of containing a drug dispersed therein; and
(b) at least one other layer comprising a second biodegradable polymer arranged adjacent the first layer.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DETAILED DESCRIPTION

Figure 1:
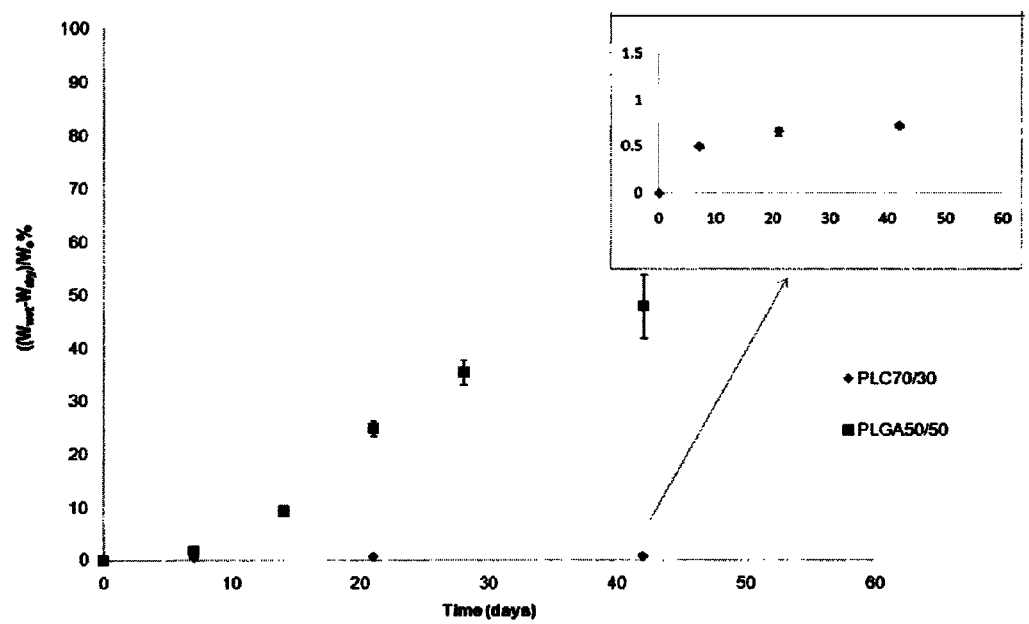
FIG. 1 shows in vitro water absorption of PLC70/30, immersed in PBS buffer (pH 7.4) of Example 1.

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

In a first aspect of the present invention, a biodegradable ocular implant is provided. The implant allows a sustained or controlled delivery of drugs and molecules for antibiotics, anti-inflammatories, anti-scarring as well as anti-glaucoma medications in ophthalmic medical therapy. Additionally, various embodiments of the present implants allow directional release of the drugs from the implants.

In various embodiments, the biodegradable ocular implant includes a first layer of a first biodegradable polymer. The first layer contains a drug dispersed or dissolved in the first layer itself.

In various embodiments, the present implant may further include at least one top layer of a second biodegradable polymer. The at least one top layer is arranged on top of the first layer. The at least one top layer may contain a drug dispersed or dissolved in the layer.

In various embodiments, the present implant may further include at least one bottom layer of a third biodegradable polymer, wherein the first layer is arranged on top of the at least one bottom layer to thereby form a sandwich assembly having the first layer arranged between the at least one top layer and the at least one bottom layer. The at least one bottom layer may contain a drug dispersed or dissolved in the layer.

In certain embodiments, the first biodegradable polymer, the second biodegradable polymer, and the third biodegradable polymer are the same. In one embodiment, the present implant has a sandwich assembly having the first, second and third biodegradable polymer being polycaprolactone or copolymer of polylactide-caprolactone.

In alternative embodiments, the first biodegradable polymer, the second biodegradable polymer, and the third biodegradable polymer are different.

Biodegradable polymers are natural or synthetic polymers that gradually degrade in vivo to produce biocompatible or non-toxic byproducts over a period of time (e.g., within days, or months, or years). Degradation may for instance occur via hydrolysis, may be catalysed by an enzyme and may be assisted by conditions to which the polymers are exposed.

Examples of biodegradable polymers include, but are not limited to, polymers and oligomers of glycolide, lactide, polylactic acid, polyesters of a-hydroxy acids, including lactic acid and glycolic acid, such as the poly(a-hydroxy) acids including polyglycolic acid, p poly(DL-lactic-co-glycolic acid) (PLGA), poly-L-lactic acid (PLLA), and terpolymers of DL-lactide and glycolide; e-caprolactone and e-caprolactone copolymerized with polyesters; polylactones and polycaprolactones including poly(caprolactone) (PCL), poly(e-caprolactone), poly(8-valerolactone) and poly (gamma-butyrolactone); polyanhydrides; polyorthoesters; other hydroxy acids; polydioxanone; and other biologically degradable polymers that are non-toxic or are present as metabolites in the body. Examples of polyaminoacids include, but are not limited to, polylysine (PLL), poly L-aspartic acid, poly L-glutamic acid, and styrene-maleic acid anhydride copolymer. Examples of derivatives of polyethylene glycol includes, but are not limited to, poly(ethylene glycol)-di-(ethylphosphatidyl(ethylene glycol)) (PEDGA), poly(ethylene glycol)-co-anhydride, poly(ethylene glycol)co-lactide, poly(ethylene glycol)-co-glycolide and poly (ethylene glycol)-co-orthoester. Examples of acrylamide polymers include, but are not limited to, polyisopropylacrylamide, and polyacrylamide. Examples of acrylate polymers include, but are not limited to, diacrylates such as polyethylene glycol diacrylate (PEGDA), oligoacrylates, methacrylates, dimethacrylates, oligomethoacrylates and PEG-oligoglycolylacrylates. Examples of carboxy alkyl cellulose include, but are not limited to, carboxymethyl cellulose and partially oxidized cellulose.

The polymers can be biocompatible. As used herein, the term "biocompatible" refers to a material that is capable of interacting with a biological system without causing cytotoxicity, undesired protein or nucleic acid modification or activation of an undesired immune response.

Some non-exhaustive examples of biocompatible polymers include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methylmethacrylate), poly (ethylmethacrylate), poly(butylmethacrylate), poly (isobutylmethacrylate), poly(hexlmethacrylate), poly (isodecylmethacrylate), poly(laurylmethacrylate), poly (phenylmethacrylate), poly(methacrylate), poly (isopropacrylate), poly (isobutacrylate), poly (octadecacrylate), polyethylene, polypropylene poly (ethylene glycol), poly(ethylene oxide), poly(ethylene terephthalate), poly(vinyl alcohols), poly(vinyl acetate) such as ethylene vinyl acetate (EVA), poly vinyl chloride, polystyrene, polyhyaluronic acids, casein, gelatin, gluten, polyanhydrides, polyacrylic acid, alginate, chitosan, any copolymers thereof, and mixtures thereof.

Each of the biodegradable polymers of the different layers may have a different degradation rate when exposed to the same physiological conditions. In various embodiments, the first layer degrades at a slower rate than any of the top or bottom layer.

In various embodiments, the biodegradable polymer may be polylactide (PLA), poly-L-lactide (PLLA), poly-D-lactide (PDLA), poly(L-lactide-co-glycolide) (PLGA), polyethylene glycol (PEG), polypropylene glycol (PPG), polycaprolactone (PCL), polyesteramide (PEA), a PLLA copolymer, a PLGA copolymer, a PDLA copolymer, a PCL copolymer, a PEA copolymer, a PEG copolymer, a PPG copolymer, or mixtures thereof.

In certain embodiments, the biodegradable polymer is a copolymer of PLA and PCL. The molar ratio PLA:PCL may be between about 90:10 and about 10:90, such as about 80:20, about 70:30, about 60:40, about 50:50.

In some embodiments, the biodegradable polymer may be a triblock copolymer comprising PLA as end-blocks and a middle block of PCL, a copolymer of PCL and trimethylene carbonate (TMC), or a copolymer of PCL and PLGA.

In yet further embodiments, the biodegradable polymer may be a multiblock copolymer of polylactide-caprolactone (PLC) and PLA.

In alternative embodiments, the biodegradable polymer may be a polyurethane type copolymer formed from diisocyanates and butanediol, and soft segments selected from PCL/PLA and PCL/TMC.

The term "drug" refers to a substance useful for the treatment of or the prevention of a human or an animal (subject) disorder or in the regulation of a human or animal physiological condition or metabolic state. In the present invention, the drug refers an ocular drug. In various embodiments, the drug may include an immunosuppressant agent, an antibiotic, an anti-inflammatory agent, an anti-scarring agent, an anti-glaucoma medication, a prostaglandin analogue, an anti-steroidal agents such as betamethasone and prednisolone, an antimicrobial agent, an anti-fibrotic antibody, or a small interfering ribonucleic acid (siRNA) molecule against fibrosis. For examples, the drug may be betamethasone, prednisolone, cyclosporine, latanoprost and derivates, timolol maleate, valproic acid, or ciproflaxin.

In some embodiments, each respective layer may include 70-98 wt % (based on total weight of the layer) of the polymer matrix and 2-30 wt % of the drug. The following list illustrates various exemplary and non-limiting drugs and the respective composition suitable for the present invention:
(i) Prednisolone acetate and other anti-inflammatories such as dexmethasone may be used for the management of post-surgical inflammation in glaucoma filtration surgery; loading of prednisolone from 1% to 30% by weight;
(ii) Timolol maleate may be used for reducing intra-ocular pressure for glaucoma patients, in a sub-cojuctival implant; timolol maleate loading from 1% to 20% by weight;
(iii) Valproic acid may be used for minimization of scarring following surgery; loading 1-5% by weight The drug may be uniformly dissolved in the polymer matrix of the respective layer of the implant. The drug is dispersed such that a homogeneous phase occurs in the respective layer so that when the layer degrades, the drug is released at a predictable rate. Erosion of the layer allows the drug to be released from the polymer matrix of the layer via diffusion initially, followed by degradation of the polymer matrix itself.

In alternative embodiments, the drug is dispersed in the layer such that a higher concentration of the drug is found at the surface of the respective layer where it starts to degrade than at the inner region of the layer away from the surface. When the surface starts to degrade, a higher concentration of the drug present at the surface is released. When the surface gets eroded over time, the concentration of the drug available in the remaining regions of the layer gets depleted and the rate of drug release slows down gradually.

In some embodiments, it may be advantageous to have the at least one top layer or the at least one bottom layer impermeable for the drug so as to provide for a directional release of the drug. In this way, diffusion and release of the drug is restricted and may provide targetted delivery of the drug.

The present implant may further include an excipient or plasticizer so as to facilitate the loading or release of the drug into the implant. For example, the excipient or plasticizer may be PEG, triethyl citrate (TEC) or glycerol.

The biodegradable ocular implant may be formable to a desired shape, such as to match the profile of the eye of a subject. The desired shape may be a curved shape or a convex shape and may be formed prior to insertion of the implant into the eye of the subject. Alternatively, the desired shape is formable after insertion into the eye of the subject. The desired shape may be formed by exposing the implant to a temperature of about 37° C. after insertion.

The present biodegradable ocular implant may have an overall thickness of about 1 mm to about 2 mm, and each of the layer may have a thickness of about 0.1 micron to about 10 microns. Advantageously, the modulus of the implant is between about 0.1 MPa and about 1,000 MPa and the elongation-to-break point of the implant is at least 300%.

A first solution containing the drug and the first biodegradable polymer is provided. The drug and the biodegradable polymer may be dissolved simultaneously in the same solvent to form the first solution. Alternatively, the drug may be dispersed in a solution containing the first biodegradable polymer to form the first solution. The solute concentration in the first solution is sufficiently high (for example, by adjusting the overall solids amount in the solution) to be able to cast a thin layer of the first solution (i.e. a casting solution) on a substrate, such as a glass substrate, without the casting solution flowing away. The casted solution with the substrate is then dried to obtain a film of the first biodegradable polymer having the drug dissolved and dispersed in the film. In one embodiment, the casted solution is placed in an oven to evaporate the solvent of the solution. The temperature of the oven may initially be set at room temperature, and gradually at elevated temperatures up to 60° C. The drying process is controlled until once the solvent level is low enough (<1% by weight), the film may be cut and used for drug release and other studies.

A top layer including a second biodegradable polymer may be similarly formed. A second casting solution containing the second biodegradable polymer solution (may also include a second drug dissolved therein) is casted on top of the first layer formed as described above. The casted solution of the second biodegradable polymer is then dried to obtain a bilayer of the top layer on top of the first layer. Further layer may then be formed of different biodegradable polymers. The layers are individually dried, so that a dried tube of a desired dimension is obtained. A strip can then be cut radially to mimic a convex shape, for example, then flattened at 25° C. or below into a flat sheet. The flat sheet may be formable to a desired shape, such as to match the profile of the eye of a subject. In one embodiment, the flat sheet is inserted into a convex mold and heated above the glass transition temperature of the biodegradable polymer in the top-most layer. At this stage, the convex shape of the implant is obtained. The implant is then cooled and stretched into a flat sheet again at 25° C. or below prior to use. By exposing the implant to a temperature of about 37° C. after insertion into the eye of the subject, the implant once again resumes the convex shape and remain intact in the eye socket.

In order that the invention may be readily understood and put into practical effect, particular embodiments will now be described by way of the following non-limiting examples.

EXAMPLES

Example 1

Biodegradable poly[d,l-lactide-co-caprolactone] (PLC) Ocular Implants

In this Example, a microfilm, poly[d,l-lactide-co-caprolactone] (PLC) was developed and evaluated for its degradation behavior in vitro and in vivo. The biocompatibility of the microfilm was evaluated. Eighteen eyes (9 rabbits) were surgically implanted with the microfilm in each eye. Serial anterior-segment optical coherence tomography (AS-OCT) scans together with serial slit-lamp microscopy allowed us to measure thickness and cross-sectional area of the microfilm. In vitro studies revealed bulk degradation kinetics for the microfilm, while in vivo studies demonstrated surface erosion kinetics. Serial slit-lamp microscopy revealed no significant inflammation or vascularization in the implants (mean increase in vascularity grade PLC (70/30) 15±0.6%; P=0.91) over a period of 6 months. Histology, immunohistochemistry and immuno-fluorescence also revealed no significant inflammatory reaction from the microfilm, which confirmed that the microfilm is biocompatible. The duration of the drug delivery can be tailored by selecting the materials, which have different degradation kinetics, to suit the desired clinical therapeutic application.

Materials and Methods

Materials

Poly(d,l-lactide-co-e-caprolactone) PLC70/30 (intrinsic viscosity 1.66 dl/g, Mw=210 kDa) was purchased from Purac Far East Pte. Ltd., Singapore. High-performance liquid chromatography (HPLC)-grade dichloromethane and chloroform were from Tedia Company. Phosphate buffer saline (PBS) tablets were obtained from CalBioChem, England.

Sample Preparation

Samples of PLC70/30 were weighed before dissolving the appropriate amount in dichloromethane. Following dissolution, the samples were dried in petri-dishes under a fume hood for a day, followed by drying in a vacuum oven at 37° C. until the solvent level was less than 1% of the total weight, as measured using a thermo-gravimetric analyzer (TGA, TA instruments Q500). After drying, all samples were cut manually into standard sized microfilms (6.0×3.0×0.5 mm) by using a sharp knife.

In Vitro Degradation Study

Samples were immersed in a closed vial containing 5 ml Phosphate Buffered Saline (PBS, pH 7.4). PBS was prepared by dissolving PBS tablets into 1 liter deionized water. All vials were incubated at 37° C. throughout the study. The buffer was refreshed every week, and at every predetermined time point, samples were taken out, rinsed with deionized water and dried in 37° C. vacuum oven for 7 days, before testing. Degradation of PLC70/30 was monitored by film thickness (measured by Elcometer 456), water absorption, weight loss and weight average molecular mass (Mw) and poly dispersity index (PDI). Dried samples were dissolved in chloroform (1-5 mg/ml) and filtered through 0.22 μm regenerated cellulose syringe driven filters before test. Weight average molar mass and poly dispersity of the sample were determined by gel permeation chromatography (GPC, Agilent 1100) at 35° C., using Agilent PLgel 5 mm mixed-C column, under a flow rate of 1 ml chloroform per minute, using a Refractive Index Detector (RID).

Sterilization

All the samples were sterilized by ethylene oxide (ETO) at 37° C. (used for normal medical device) in Tan Tock Seng Hospital (Singapore) prior insertion into animals.

Surgical Insertion of Microfilms

We obtained approval from the SingHealth Institute Animal Care and Use Committee (IACUC Singhealth Approval Number 2009/SHS/478) and all procedures were performed in accordance with the ARVO Statement for the Use of Animals in Ophthalmic and Vision Research. Nine New Zealand white rabbits (18 eyes) were used aged 4-6 months old with a weight range of 2-2.5 kg each. Each rabbit was anesthetized with intraperitoneal injection of ketamine hydrochloride (35-50 mg/kg) and Xylazil (5-10 mg/kg). After the animal had been adequately anaesthetized, the eye was cleaned with povidone-iodine (10%) and draped with sterile cloth. A subconjunctival pocket was created via blunt dissection just at the limbus with a 5-6 mm incision in the superior-temporal aspect of the rabbit's eye. Microfilms were sterilized in ethyl alcohol and chlorhexidine before soaking in sterile normal saline. The microfilm was then inserted into the subconjunctival pocket 1 mm from the limbus using a conjunctival forceps. Closure with 10-0 nylon sutures was done to ensure secure implantation of each microfilm. In each rabbit, PLC70/30 (n=9) microfilms were inserted into the right eye. Topical Tobradex (Tobramycin & Dexamethasone) was administered each eye 4 times a day for 5 days.

Clinical Monitoring

Visual inspection of the operated eyes was conducted daily following surgery. The animals' eyes were also inspected for changes at the insertion site, gross appearance of the implant and for any evidence of infection. Slit-lamp examination of the exterior and anterior chamber of the eyes was done prior to surgery and weekly thereafter. All clinical and ocular observations were recorded on a chart. The test animals were also monitored for any gross changes such as eye discharge, squinting and, ocular discomfort. A modified Hackett McDonald ocular score was used to record the presence of conjunctival injection, swelling, discharge and corneal clarity. Two masked independent investigators (MA, TTW) objectively graded each eye based on slit lamp photography.

Anterior Segment Optical Coherence Tomography

Anterior segment photographs and anterior segment optical coherence tomography (AS-OCT, Visante OCT, Carl Zeiss Meditec Inc., Germany) of the implanted eyes was performed at monthly intervals. The Visante OCT is a high-resolution biomicroscopic device for anterior segment imaging (axial resolution=18 mm), based the principle of low coherence interferometry using a 1310 nm light emitting diode. Due to the optical properties of different tissues, the AS-OCT image can help us identify internal structures of the eye, such as fluid, scarring or thinning of the sclera or conjunctiva. We used a modified technique previously described to obtain standardized images of the implanted microfilm in each rabbit eye by a single, masked operator (WSL). A radial anterior segment line scan was chosen to include both the implanted microfilm and the surgical insertion site. The site of conjunctival elevation from the microfilm was determined by the location of a light reflex over the conjunctiva during image acquisition. In cases where the light reflex was absent, the observer manually assessed the surface of the microfilm to select a radius that contained elevation. This ASOCT technique allowed us to image the layers of the eye, location of implant as well as obtain standardized measurements of the implant, which was included microfilm thickness and length. The Anterior Segment OCT (AS-OCT) is calibrated internally to detect internal structures of the eye using high-resolution corneal and angle scans and pachymetry maps at a rate of up to 2048 A-scans per second, with an optical axial resolution of up to 18 mm and optical transverse resolution of up to 60 mm (Carl Zeiss Meditec Inc, www.meditec.zeiss.com).

Results

In Vitro Degradation Study

Various factors in vitro, such as water absorption, weight loss, change in thickness and change in molar mass, were studied to analyze the degradation of both types of microfilms.

Water absorption. As these polymers degrade in the body by simple hydrolysis, water absorption rates are indicative of hydrolysis rates. The amount of water absorbed by the sample was calculated as: Water absorption=$(W_{wet}-W_{dry})/W_o$ %, where $W_{wet}$ represents the weight of the wet sample after wiping by tissue, $W_{dry}$ represent the final weight of the dried samples, and $W_o$ represent the sample's initial weight. The amount of water absorbed in the microfilm increased with immersion time for both polymers (FIG. 1). PLC70/30 absorbed only about 1% of water over 6 weeks. This was primarily due to PLC70/30 is semi-crystalline, and water absorption is limited to the amorphous phase.

Figure 2:
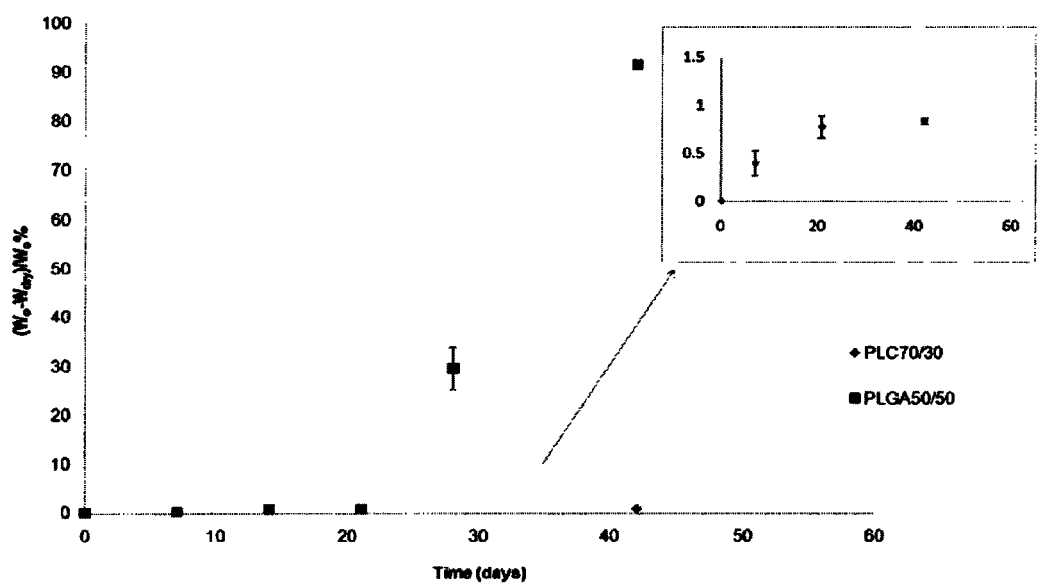
FIG. 2 shows in vitro weight loss of PLC70/30, immersed in PBS buffer (pH 7.4) of Example 1.

Mass loss. Mass loss was calculated as: $(W_o-W_{dry})/W_o$ %. In conjunction with water absorption, PLC 70/30 did not demonstrate any notable mass loss until after day 56 (FIG. 2). PLC had absorbed very little water and hence the observed hydrolysis rate was low, with water-soluble oligomers not forming to any measurable extent until day 56.

Figure 3:
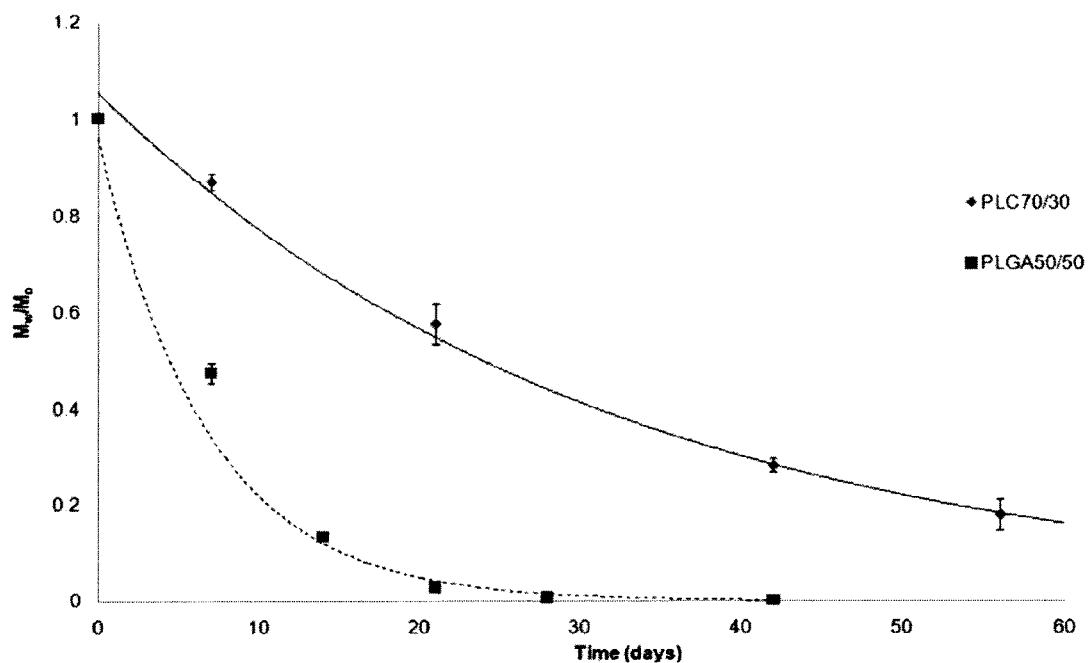
FIG. 3 shows the monitoring of weight molecular mass for PLC70/30 in vitro (PBS, pH 7.4) of Example 1.

Change of molecular weight (Mw) and PDI. There was a notable decrease in weight molecular mass for PLC70/30 over 56 days (FIG. 3). The $M_w/M_o$ versus time graph showed that the polymer demonstrated bulk degradation with a thickness of 0.5 mm, and the drop in Mw agreed with the corresponding water absorption and mass loss.

Figure 4:
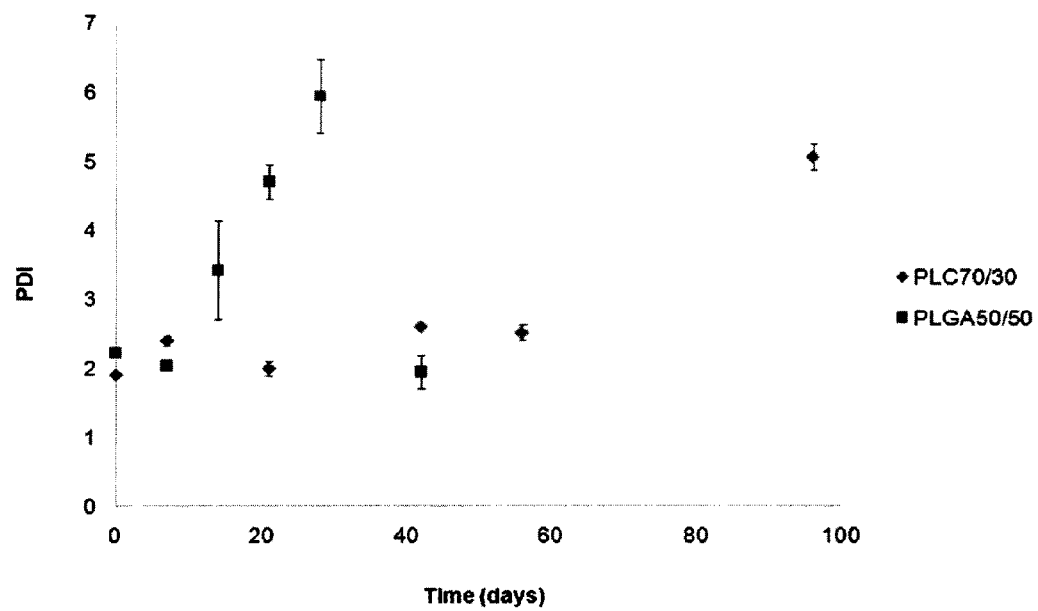
FIG. 4 shows the monitoring of PDI for PLC70/30 in vitro (PBS, pH 7.4) of Example 1.

As shown in FIG. 4, PDI of the samples increased with time. PDI for PLC70/30 increased slightly in the first 56 days of study, but increased suddenly to 5 or more at the end of the study (not fully degraded at the end of the study period).

Figure 5:
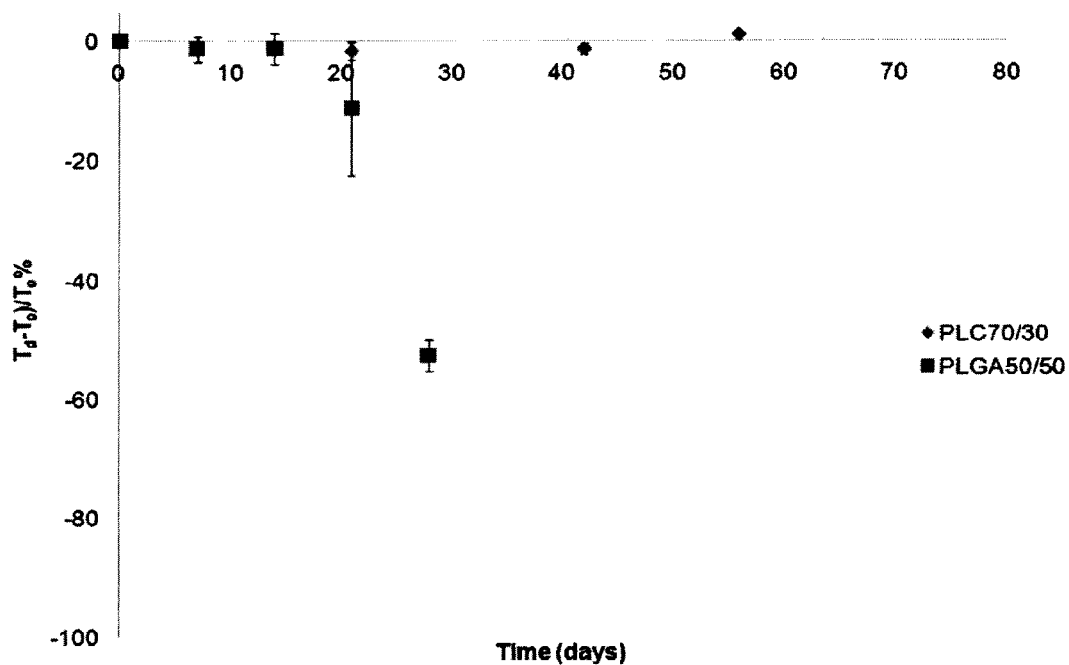
FIG. 5 shows the change of film thickness of PLC70/30 in vitro (PBS, pH 7.4) of Example 1.

Thickness change with degradation. PLC70/30 maintained its shape throughout the entire duration of the study period, with minimal change in film thickness (FIG. 5).

Results of In Vivo Study in Rabbit Eyes

Figure 6:
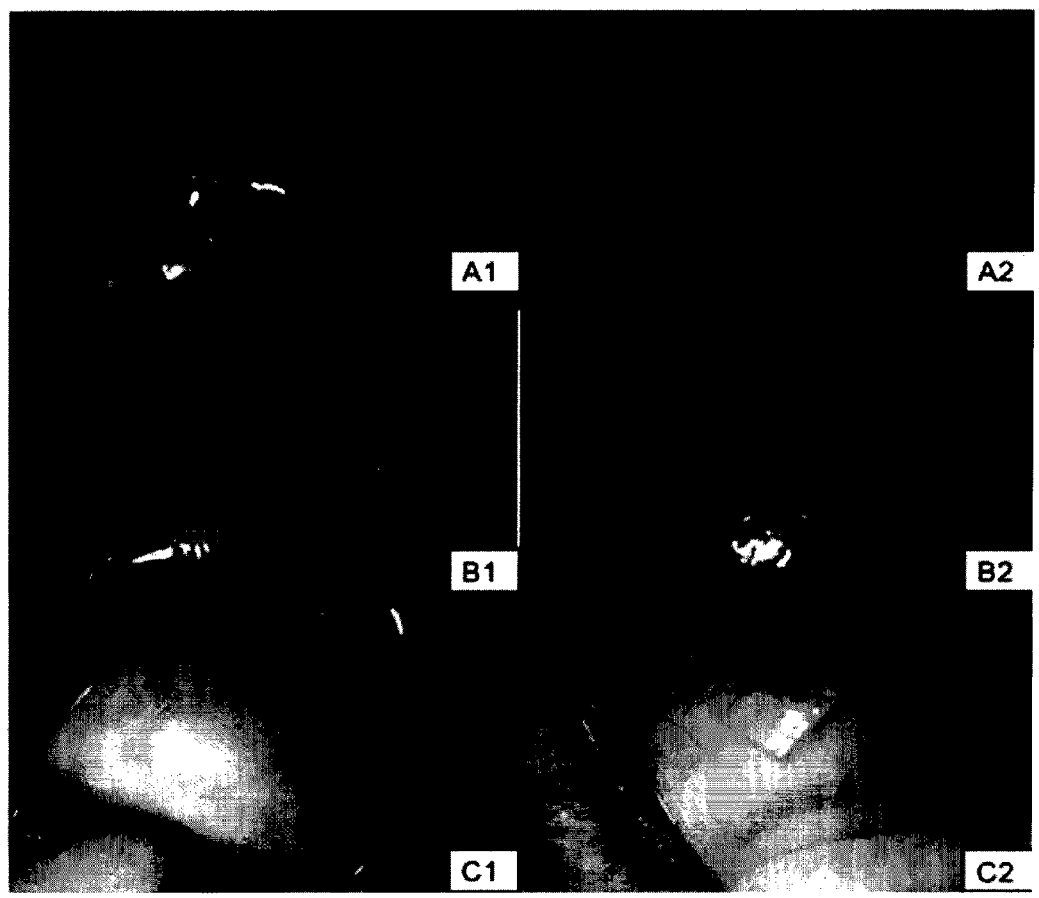
FIG. 6 shows slit-lamp photographs of microfilms of Example 1 after surgical insertion into the subconjunctival space at 1, 3 and 6 months. A, B, C: 1—Slit-lamp photographs of PLGA50/50 microfilm at 1, 3, 6 months respectively. A, B, C: 2—Slit-lamp photograph of PLC70/30 microfilm at 1, 3, 6 months respectively.

Slit-lamp examination of implanted microfilms. The gross appearance and examination of the implanted microfilms revealed minimal localized inflammation and vascularity using serial vascularity grading scales around the implanted PLC70/30 (n=9). The eyes had mild conjunctival hyperemia and chemosis, which resolved at one week post-operatively (FIG. 6). Conjunctival vascularity of the insertion site before surgery and at the end of the study in all eyes was compared. It was found no significant increase in ocular score in the eyes (mean percent increase in ocular score PLC70/30 15±0.6%; P=0.91, no significant inter-observer variability). The cornea, anterior chamber and lens remained clear with no evidence of inflammation or scarring. We did notice on external ocular examination that the PLC70/30 microfilms retained its original shape. PLC70/30 microfilms persisted and remained visible up to 6 months.

Figure 7:
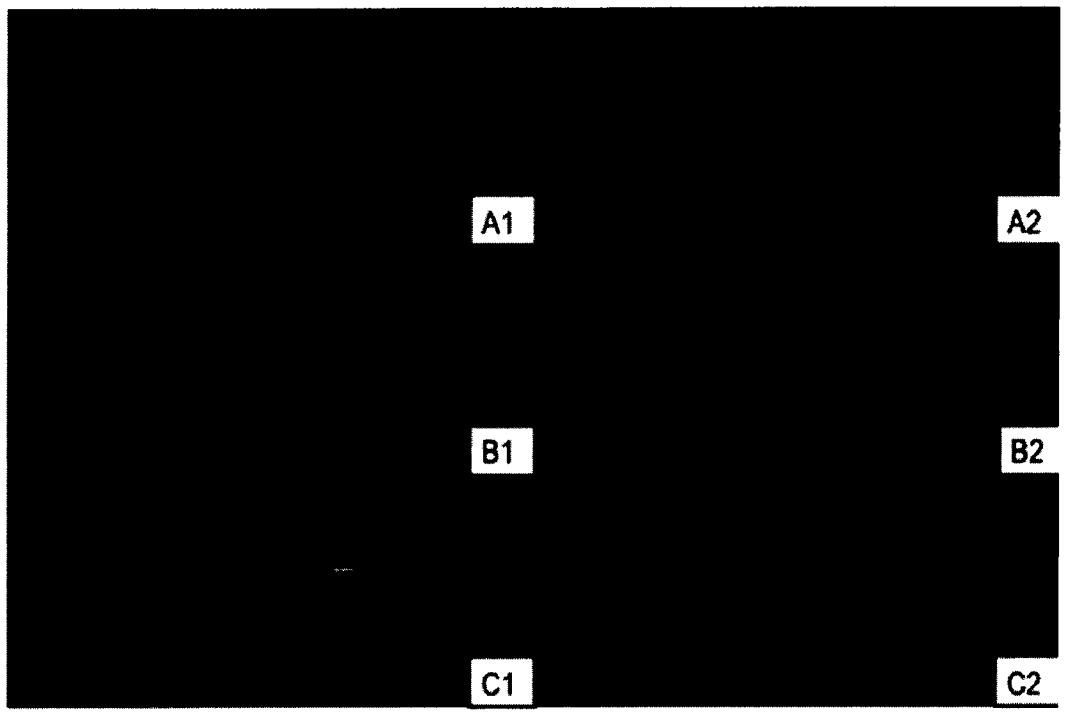
FIG. 7 shows the AS-OCT scans of microfilms after subconjunctival implantation of Example 1.
Figure 8:
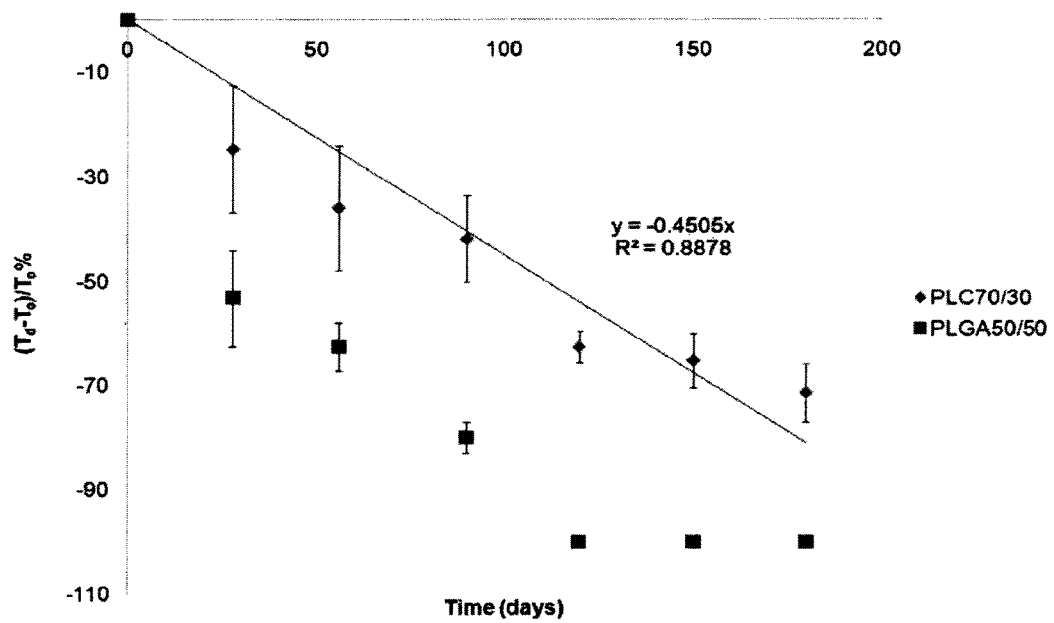
FIG. 8 shows the serial AS-OCT thickness measurements of PLC70/30 microfilms in subconjunctival space of Example 1.

Anterior Segment Optical Coherence Tomography (ASOCT) scans. The AS-OCT images taken at monthly intervals revealed good anatomical placement of all microfilms implanted in the subconjunctival space (FIG. 7). No migration from the original surgically implanted site was seen in any of the implants. There was no evidence of scleral erosion of the subconjunctival implants in any of the eyes. Serial measurements were taken from the AS-OCT images that measured multiple sections of the implanted microfilms. We found that the thickness of the PLC microfilms decreased, and PLC70/30 decreased in a linear fashion (R2=0.8878 for PLC70/30), as measured by AS-OCT (FIG. 8).

Discussion

The current mainstay of ocular therapy is via topical administration. While it is easy to administer (for example, using eye drops), there are many drawbacks—which include poor bioavailability and penetration of the drugs, frequent instillation leading to poor compliance and blurring of vision from viscous vehicles. Typically less than 5% of the topically applied drug penetrates the cornea and reaches intraocular tissues, while a major fraction of the instilled dose is often absorbed systemically via the conjunctiva and nasolacrimal duct. Thus, frequent instillation of a relatively concentrated solution is required for a sustained, therapeutic effect. This need for frequent instillation also leads to poor patient compliance, with often disastrous consequences for vision.

Biodegradable polymers were used to create implants that may be capable of sustained ocular drug delivery, to overcome the disadvantages of topical medications and the issues with compliance—a common problem faced by ophthalmologists in dealing with diseases such as glaucoma, the second leading cause of irreversible blindness in the world. This biopolymer microfilm placed in the subconjunctival space may significantly improve drug availability and reduce local ocular side effects, while overcoming poor patient compliance.

It is generally accepted that, in this class of polymers used in the study (poly α-hydroxy esters), there may be two different modes of degradation. In the first mechanism, which is often referred to as homogeneous or bulk degradation, the polymers degrade slowly with no appreciable mass or volume loss until the degradation products become water-soluble and leach out of the matrix, when mass loss is then detectable. In the second mechanism, the polymer degrades first at the surface, and the surface molecules decrease in molecular weight to the point where the surface molecules leach out, without affecting the interior of the material. In this mode of degradation, which is sometimes referred to as heterogeneous degradation or surface erosion, there is continuous decrease in mass and in the material dimensions.

From the results of the study, although not as evident (since no significant mass loss has been detected up to day 40—FIG. 2), in vitro, PLC70/30 also exhibited molecular weight decrease (FIG. 3) without any mass loss, which is a characteristic of bulk degradation. However, PLC70/30 clearly behaves differently when implanted into the rabbit eyes. PLC70/30 microfilms underwent surface erosion in the subconjunctival space, as evidenced by our serial measurements using slit-lamp microscopy and AS-OCT techniques, since the width and length of the microfilms did not change visually over 6 months (FIG. 6), but thickness of the films (FIG. 7) decreased continuously. This is typically observed in surface erosion or heterogeneous degradation. Usually, the polymer changes from a bulk degradation mode to a surface erosion mode when the intrinsic hydrolysis rate ($R_h$) becomes higher than the water ingress rate into the polymer ($R_w$). It is hypothesized that in the in vivo situation, $R_h$ is being increased relative to $R_w$, most likely due to the influence of enzymes (esterases) or proteins present in the eye. A surface erosion mode is the preferred mode in such applications, as bulk degradation may lead to "catastrophic" breakdown into small fragments causing localized irritation. Surface erosion also results in a constant release of incorporated drug. PLC are anionic polymers that undergo bulk degradation in vitro. Embedded drugs are released from the matrix via diffusion initially, followed by degradation of the polymer matrix itself. Thus the first observation of surface erosion of this grade of polymers in the subconjunctival space is exciting and opens the door for a more efficient therapeutic route.

The subconjunctival space is a potential area in the eye that is useful for delivering ocular drugs in a sustained manner. Currently, peribulbar or subtenon injections are used to deliver short to intermediate duration of drugs to the eye. Implanting the microfilm in this space may bypass ocular blood and lymphatic barriers, to achieve therapeutic levels in the eye with lower loading concentrations of drug. In this study, we have shown that the PLC70/30 microfilms can be placed into the subconjunctival space using a simple surgical technique, and that both microfilms remain stable in-situ for up to 6 months. Furthermore, we have demonstrated that surgical implantation of these films in the subconjunctival space does not cause any associated significant scarring, encapsulation or inflammation. The biodegradable microfilms prepared from PLC70/30 are non-toxic and well tolerated when implanted in the subconjunctival space and therefore has the potential use as an ocular drug delivery platform. PLC70/30 demonstrated bulk degradation in vitro, whereas PLC70/30 exhibited surface erosion in vivo. The observation of surface erosion in the sub-conjunctival space is significant for controlling the release of drugs locally, and opens the door for more efficient and sustained therapy.

Example 2

Figure 9:
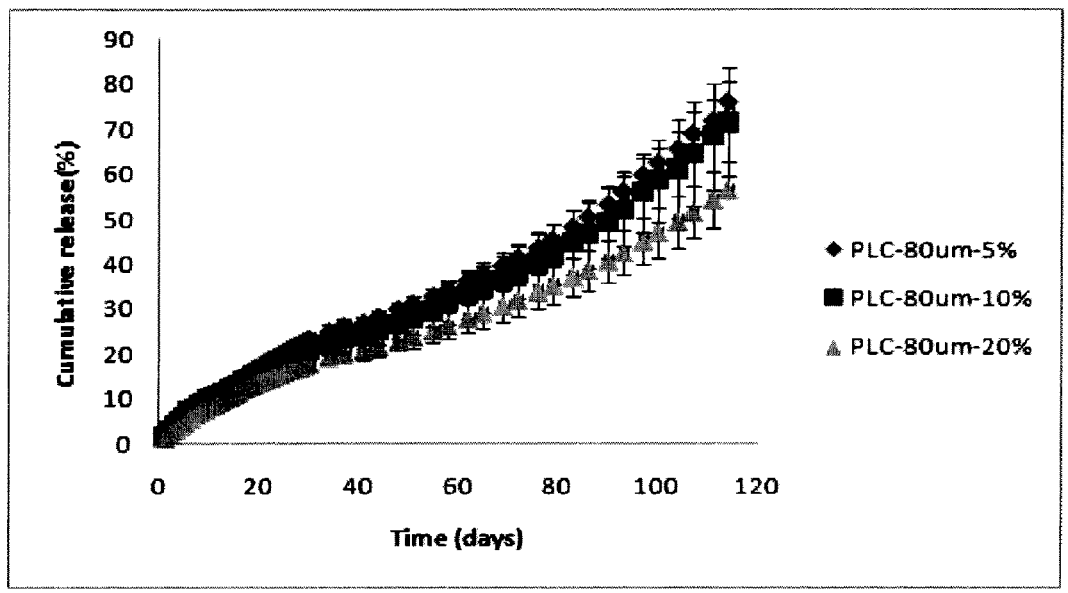
FIG. 9 shows sustained release profile of prednisolone of Example 2.
Figure 10:
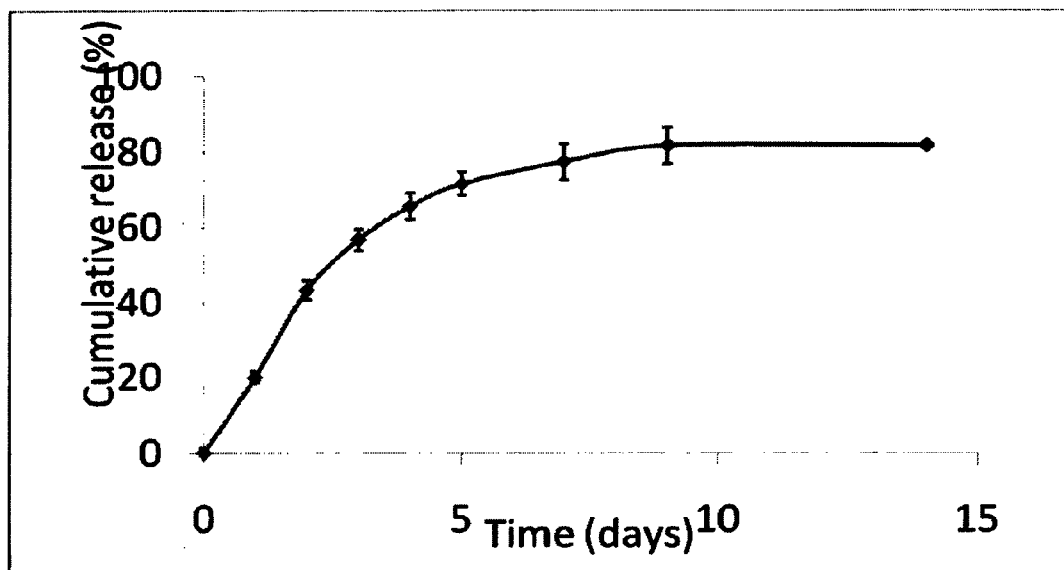
FIG. 10 shows sustained release profile of latanoprost of Example 2.

Biodegradable Copolymer of Polylactide (PLA) and Polycaprolactone (PCL) Drug-Eluting Ocular Implants Biodegradable copolymer of PLA and PCL (PLC) layers can be formulated with drugs to achieve sustained release over several days.
Prednisolone Release
Prednisolone release from PLC (70/30 copolymer of PLA and PCL) is released in a controlled manner over 100 days, and is very useful for post-surgical management of inflammation in glaucoma filration surgery. See FIG. 9.
Latanoprost Release
Latanoprost, an anti-glaucoma medication used for reducing intra-ocular pressure in the eye, may be delivered for 10 days from PLC films. See FIG. 10.

Example 3

Multi-layered Biodegradable Drug-Eluting Ocular Implants Valproic Acid Release

Figure 11:
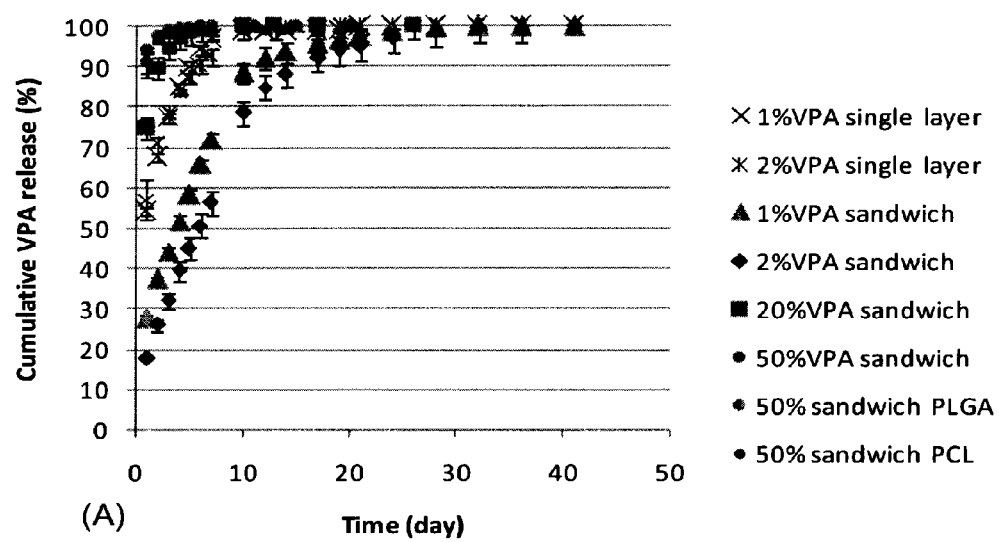
FIG. 11 shows (A) sustained release profile of valproic acid and (B) sandwich assembly of a multi-layered implant of Example 3.
Figure 11:
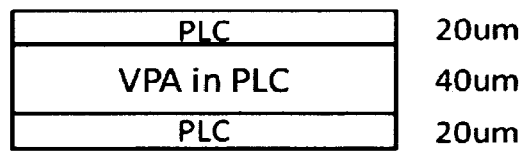

The release may be extended by using sandwich constructions, as shown in FIG. 11(A). For compatibility reasons, it is preferred that the outermost layers be made from PLC, but the inner drug-containing layers may be made from polymers such as PLGA 50/50, PLGA 75/25, and the copolymers mentioned above. A drug, valproic acid, used for management of scarring following optical surgery, can be released in a controlled manner from the sandwich constructions (see FIG. 11). Of the curves shown, only the 1% and 2% sandwich constructions are acceptable in terms of controlled release over 20 days.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numberical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. A biodegradable ocular implant for sustained drug delivery, comprising a first layer comprising a first biodegradable polymer, wherein the first layer contains a drug dispersed or dissolved therein.

2. The biodegradable ocular implant of claim 1, further comprising at least one top layer comprising a second biodegradable polymer, wherein the at least one top layer is arranged on top of the first layer.

3. The biodegradable ocular implant of claim 2, further comprising at least one bottom layer comprising a third biodegradable polymer, wherein the first layer is arranged on top of the at least one bottom layer to thereby form a sandwich assembly having the first layer arranged between the at least one top layer and the at least one bottom layer.

4. The biodegradable ocular implant of claim 3, wherein the at least one top layer, or the at least one bottom layer, or both, contains a drug dispersed or dissolved in the respective layer.

5. The biodegradable ocular implant of claim 1, wherein the drug is uniformly dissolved in the polymer matrix of the respective layer.

6. The biodegradable ocular implant of claim 1, wherein the drug is dispersed at the surface of the respective layer.

7. The biodegradable ocular implant of claim 3, wherein the first biodegradable polymer, the second biodegradable polymer, and the third biodegradable polymer are the same.

8. The biodegradable ocular implant of claim 3, wherein the first biodegradable polymer, the second biodegradable polymer, and the third biodegradable polymer are different.

9. The biodegradable ocular implant of claim 1, wherein each biodegradable polymer is independently selected from the group consisting of polylactide (PLA), poly-L-lactide (PLLA), poly-D-lactide (PDLA), poly(L-lactide-co-glycolide) (PLGA), polyethylene glycol (PEG), polypropylene glycol (PPG), polycaprolactone (PCL), polyesteramide (PEA), a PLLA copolymer, a PLGA copolymer, a PDLA copolymer, a PCL copolymer, a PEA copolymer, a PEG copolymer, a PPG copolymer, and mixtures thereof.

10. The biodegradable ocular implant of claim 9, wherein the biodegradable polymer is a copolymer of PLA and PCL.

11. The biodegradable ocular implant of claim 10, wherein the molar ratio PLA:PCL is between about 90:10 and about 10:90.

12. The biodegradable ocular implant of claim 11, wherein the molar ratio PLA:PCL is 70:30.

13. The biodegradable ocular implant of claim 9, wherein the biodegradable polymer is a triblock copolymer comprising PLA as end-blocks and a middle block selected from the group consisting of PCL, a copolymer of PCL and trimethylene carbonate (TMC), a copolymer of PCL and PLGA.

14. The biodegradable ocular implant of claim 9, wherein the biodegradable polymer is a multiblock copolymer of polylactide-caprolactone (PLC) and PLA.

15. The biodegradable ocular implant of claim 9, wherein the biodegradable polymer is a polyurethane type copolymer formed from di-isocyanates and butanediol, and soft segments selected from PCL/PLA and PCL/TMC.

16. The biodegradable ocular implant of claim 3, wherein the at least one top layer or the at least one bottom layer is impermeable for the drug to provide for a directional release of the drug.

17. The biodegradable ocular implant of claim 2, wherein each of the biodegradable polymers of the different layers has a different degradation rate.

18. The biodegradable ocular implant of claim 1, wherein the drug comprises an ocular drug.

19. The biodegradable ocular implant of claim 1, wherein the drug is selected from the group consisting of an immunosuppressant agent, an antibiotic, an anti-inflammatory agent, an anti-scarring agent, an anti-glaucoma medication, a prostaglandin analogue, an anti-steroidal agents, an anti-microbial agent, an anti-fibrotic antibody, and a small interfering ribonucleic acid (siRNA) molecule against fibrosis.

20. The biodegradable ocular implant of claim 19, wherein the drug is betamethasone, prednisolone, dexmethasone, cyclosporine, latanoprost and derivates, timolol maleate, valproic acid, or ciproflaxin.

21. The biodegradable ocular implant of claim 1, wherein each respective layer comprises 70-98 wt % (based on total weight of the layer) of the polymer matrix and 2-30 wt % of the drug.

22. The biodegradable ocular implant of claim 1, wherein the modulus of the biodegradable ocular implant is between about 0.1 MPa and about 1,000 MPa.

23. The biodegradable ocular implant of claim 1, wherein the elongation-to-break point of the biodegradable ocular implant is at least 300%.

24. The biodegradable ocular implant of claim 1, further comprising an excipient or plasticizer.

25. The biodegradable ocular implant of claim 24, wherein the excipient or plasticizer is PG, triethyl citrate (TEC) or glycerol.

26. The biodegradable ocular implant of claim 1, wherein the biodegradable ocular implant is a multi-layer film comprising the first layer, the multi-layer film being configured to be implanted within a subconjunctival space of an eye of a subject.

27. The biodegradable ocular implant of claim 26, wherein the biodegradable ocular implant is configured to resume a desired shape after insertion into the subconjunctival space of the eye of the subject.

28. The biodegradable ocular implant of claim 27, wherein the desired shape comprises a curved shape or a convex shape.

29. The biodegradable ocular implant of claim 27, wherein the biodegradable ocular implant is configured to resume the desired shape when exposed to a temperature of about 37° C.

30. The biodegradable ocular implant of claim 1, wherein each of the layers has a thickness of about 0.1 micron to about 10 microns.

31. The biodegradable ocular implant of claim 1, wherein the biodegradable ocular implant has an overall thickness of about 1 mm to about 2 mm.

32. A method of forming a biodegradable ocular implant for sustained drug delivery, comprising:
(a) providing a first layer comprising a first biodegradable polymer; and
(b) loading the first biodegradable polymer with a drug.

33. The method of claim 32, wherein providing the first layer comprises:
(a) dissolving the first biodegradable polymer in a suitable solvent to form a first solution; and
(b) evaporating the solvent to obtain the first layer.

34. The method of claim 33, wherein loading comprises adding the drug to the first solution prior to evaporating the solvent.

35. The method of claim 32, wherein loading comprises immersing the first layer in a solution containing the drug.

36. The method of claim 33, wherein loading comprises simultaneously dissolving the drug and the first biodegradable polymer in the solvent prior to evaporating the solvent.

37. The method of claim 32, further comprising:
(a) dissolving a second biodegradable polymer with a suitable solvent to form a second solution;
(b) casting the second solution on top of the first layer; and
(c) evaporating the solvent to form a top layer.

38. The method of claim 32, further comprises forming a bottom layer on which the first layer is arranged, comprising:
(a) dissolving a third biodegradable polymer with a suitable solvent to form a third solution;
(b) evaporating the solvent to form a bottom layer; and
(c) depositing the first layer on top of the bottom layer.

39. The method of claim 38, wherein the first layer, or the top layer, or the bottom layer is formed over a curved-surfaced member.

40. The method of claim 39, wherein the curved-surfaced member comprises a tubular scaffold or a cylinder.

41. The method of claim 39, further comprising cutting the respective layer radially to obtain a convex shape.

42. The method of claim 38, wherein the first layer, or the top layer, or the bottom layer is casted into a convex mold to obtain a convex shape.

43. The method of claim 38, wherein the first layer, or the top layer, or the bottom layer is casted into a flat sheet, followed by heat-shaping the flat sheet into a convex shape.

44. The method of claim 43, wherein the biodegradable ocular implant comprises an outermost layer and wherein the heat-shaping step is applied to the outermost layer at its glass transition temperature (Tg).

45. A method for treating an ocular disease or reducing preoperative effects of multiple quadrant corneal vascularization or improving corneal graft survival, comprising implanting a biodegradable ocular implant for sustained drug delivery to a subject in need thereof, the biodegradable ocular implant comprising a first layer comprising a first biodegradable polymer, wherein the first layer contains a drug dispersed or dissolved therein.

46. The method of claim 45, wherein the ocular disease is an ocular surface disease selected from the group consisting of vernal keratoconjunctivits and allergic eye disease.

47. The method of claim 45, wherein the biodegradable ocular implant is a multi-layer film comprising the first layer, and the multi-layer film is implanted within a subconjunctival space of an eye of the subject.

48. A biodegradable ocular implant for sustained drug delivery, comprising a first layer comprising a first biodegradable polymer matrix capable of containing a drug dispersed therein.

49. A multi-layered biodegradable ocular implant for sustained drug delivery, comprising:
(a) a first layer comprising a first biodegradable polymer capable of containing a drug dispersed therein; and
(b) at least one other layer comprising a second biodegradable polymer arranged adjacent the first layer.

50. The multi-layered biodegradable ocular implant of claim 49, wherein the second biodegradable polymer is capable of containing a drug dispersed therein.

51. The method of claim 32, wherein the biodegradable ocular implant is a multi-layer film comprising the first layer, and the method comprises forming the multi-layer film to be configured to be implanted within a subconjunctival space of an eye of a subject.

52. The biodegradable ocular implant of claim 48, wherein the biodegradable ocular implant is a multi-layer film comprising the first layer, the multi-layer film being configured to be implanted within a subconjunctival space of an eye of a subject.

53. The multi-layered biodegradable ocular implant of claim 49, wherein the multi-layered biodegradable ocular implant is a multi-player film comprising the first layer and the at least one other layer, the multi-layer film being configured to be implanted within a subconjunctival space of an eye of a subject.

* * * * *

UNITED STATES PATENT AND TRADEMARK OFFICE
CERTIFICATE OF CORRECTION

PATENT NO. : 9,782,346 B2
APPLICATION NO. : 14/862963
DATED : October 10, 2017
INVENTOR(S) : Venkatraman et al.

It is certified that error appears in the above-identified patent and that said Letters Patent is hereby corrected as shown below:

In the Claims

Column 16,
Line 30, Claim 53 "multi-player film" should read --multi-layer film--.

Signed and Sealed this
Twenty-seventh Day of February, 2018

Andrei Iancu
*Director of the United States Patent and Trademark Office*